US006455537B1

(12) United States Patent
Cooper

(10) Patent No.: US 6,455,537 B1
(45) Date of Patent: Sep. 24, 2002

(54) METHODS FOR TREATING OPIATE INTOLERANCE

(76) Inventor: Barrett R. Cooper, 5018 Dresden Dr., Durham, NC (US) 27707

( * ) Notice: Subject to any disclaimer, the term of this patent is extended or adjusted under 35 U.S.C. 154(b) by 0 days.

(21) Appl. No.: 09/648,496

(22) Filed: Aug. 25, 2000

Related U.S. Application Data

(60) Provisional application No. 60/150,739, filed on Aug. 25, 1999.

(51) Int. Cl.$^7$ .................. A61K 31/44; A61K 31/415
(52) U.S. Cl. .................. 514/289; 514/299; 514/397
(58) Field of Search .................. 514/289, 299, 514/397

(56) References Cited

U.S. PATENT DOCUMENTS

| | | | |
|---|---|---|---|
| 3,254,088 A | 5/1966 | Lewenstein et al. ........ 260/285 |
| 3,773,955 A | 11/1973 | Pachter et al. .............. 424/260 |
| 4,466,968 A | 8/1984 | Bernstein ................... 424/260 |
| 4,719,215 A | 1/1988 | Goldberg .................... 514/282 |
| 5,756,514 A | 5/1998 | Larijani .................... 514/299 |
| 5,854,270 A | * 12/1998 | Gambhir .................... 514/397 |

FOREIGN PATENT DOCUMENTS

| | | | |
|---|---|---|---|
| CA | 1 220 200 | 4/1987 | C07D/221/28 |
| EP | 0 113 632 | 12/1982 | C07D/221/28 |
| WO | WO 99/22737 | 5/1999 | A61K/31/485 |

OTHER PUBLICATIONS

Kiang et al.; "Tolerance to Morphine Bradycardia in the Rat" *The Journal of Pharmacology and Experimental Therapeutics* 226:1 187–191 (1983).

Adcock et al.; Effects of codeine, morphine and a novel opioid pentapeptide BW443C on cough, nociception and ventilation in the unanaesthetized guiniea–pig, *Br. J. Pharmacol.* 93 93–100 (1988).

Adcock; Peripheral opioid receptors and the cough reflex, *Respiratory Medicine* 85 43–46 (1991).

Bernáth et al.; Optical Rotatory Dispersion of Some Morphine and Codeine Derivatives, *Acta Chimica Academiae Scientiarum Hungaricae Tomus* 51:3 339–348 (1967).

Bianchetti et al.; Quaternary Derivatives of Narcotic Antagonists: Sterochemical Requirements at the Chiral Nitrogen for In Vitro and In Vivo Activity, *Life Sciences* 33:I 415–418 (1983).

Bianchi et al.; Quaternary Narcotic Antagonists' Relative Ability to Prevent Antinociception and Gastrointestinal Transit Inhibition in Morphine–Treated Rats as an Index of Peripheral Selectivity, 30:22, 1875–1883 (1982).

Brown et al.; The Use of Quaternary Narcotic Antagonists in Opiate Research, *Neuropharmacology* 24:3 181–191 (1985).

Clark et al.; Opiate–induced inhibition of the visceral distention reflex by peripheral and central mechanisms, *Naunyn–Schmiedeberg's Arch Pharmacol* 330 179–183 (1985).

Clark et al.; Evaluation of opioid–induced antinociceptive effects in anaesthetized and conscious animals, *Br. J. Pharmacol.* 95 275–283 (1988).

De Oliveira et al.; Quaternary Ammonium Salt Derivatives of Allylphenols with Peripheral Analgesic Effect, *Mem. Inst. Oswaldo Cruz* 86:II 133–136 (1991).

Dragonetti et al.; Levallorphan Methyl Iodide (SR 58002), A Potent Narcotic Antagonist with Peripheral Selectivity Superior to that of Other Quaternary Compounds, *Life Sciences* 33:I 477–480 (1983).

Esplugues et al.; Morphine Potentiation of Ethanol–Induced Gastric Mucosal Damage in the Rat, *Gastroenterology* 98 82–89 (1990).

Esplugues et al.; Modulation by peripheral opioids of basal and distension–stimulated gastric acid secretion in the rat, *Br. J. Pharmacol.* 106 33–38 (1992).

Ferreira et al.; Is Methylnalorphinium the Prototype of an Ideal Peripheral Analgesic?, *European Journal of Pharmacology* 99 23–29 (1984).

Foss et al.; Dose–Related Antagonism of the Emetic Effect of Morphine by Methylnaltrexone in Dogs, *J. Clin Pharmacol* 33 747–751 (1993).

Hardy et al.; Peripherally Acting Enkephalin Analogues, *J. Med. Chem.* 32:5 1108–1118 (1989).

Hein et al.; Pharmacological Analysis of the Discriminative Stimulus Characteristics of Ethylketazocine in the Rhesus Monkey, *The Journal of Pharmacology and Experimental Therapeutics* 218:1 7–15 (1981).

Holbrook et al.; The effect of N–methyl nalorphine on opiate–induced delay in upper gastrointestinal transit in healthy volunteers, *Proceedings of the BPS*, 14–16 169P (1993).

Iorio et al.; TLC Behaviour of quaternary Ammonium Halides on Silica Gel, *II Farmaco—Ed. Pr.* 38:3 126–132 (1982).

Iorio et al.; Diastereoisomeric quaternary morphinium salts: synthesis, stereochemistry and analgesic properties, *Eur. J. Med. Chem.* 19:1 11–16 (1984).

Kobylecki et al.; Communications to the Editor: N–Methylnalorphine: Definition of N–Allyl Conformation for Antagonism at the Opiate Receptor, *American Chemical Society* 25 1278–1280 (1982).

(List continued on next page.)

Primary Examiner—Zohreh Fay
Assistant Examiner—Biran-Yong Kwon
(74) *Attorney, Agent, or Firm*—Myers Bigel Sibley & Sajovec, P.A.

(57) ABSTRACT

Provided are compositions comprising an opiate analgesic and an active compound containing the R isomer of N-methylnalorphine in a pharmaceutically acceptable carrier. Also provided are methods of treating opiate intolerance by administration of an active compound containing R N-methylnalorphine or a pharmaceutically acceptable salt thereof. The active compound may administered either acutely or chronically to subjects receiving opiate treatment. Further provided are methods of inducing analgesia by administering to a subject an opiate analgesic concurrently with an active compound containing R N-methylnalorphine or a pharmaceutically acceptable salt thereof.

13 Claims, 2 Drawing Sheets

OTHER PUBLICATIONS

Koczka et al.; Selective Quaternization of Compounds with Morphine Skeleton, *Acta Chimica Acedemiae Scientiarum Hungaricae* 51 393–402 (1967).

Kosterlitz et al.; Rates of Onset and Offset of Action of Narcotic Analgesics in Isolated Preparations, *European Journal of Pharmacology* 32 10–16 (1975).

Lamande et al.; Structure–activité des analgésiques morphiniques. III. Complexes á transfert de charge obtenus á partir de la morphine et de ses dérivés, *Eur. J. Med. Chem.—Chimica Therapeutica* 11:5 419–425 (1976).

Lorenzetti et al.; The Analgesic Effect of Quaternary Analogues of Morphine and Nalorphine, *Brazilian J Med Biol Res* 15 285–290 (1982).

Magnan et al.; The Binding Spectrum of Narcotic Analgesic Drugs with Different Agonist and Antagonist Properties, *Naunyn–Schmiedeberg's Arch Pharmacol* 319 197–205 (1982).

Musacchio et al.; Dextromethorphan and Sigma Ligands: Common Sites but Diverse Effects, *Life Sciences* 45:19 1721–1732 (1989).

Notarnicola et al.; Relative Ability of N–Methyl Nalorphine and N–Methyl Levallorphan to Prevent Antinociception and Intestinal Transit Inhibition in Morphine Treated Rats, *Life Sciences* 33:I 481–484 (1983).

Smith et al.; Peripheral Aminociceptive Effects of N–Methyl Morphine, *Life Science* 31:12 and 13 1205–1208 (1982).

Smith et al.; Peripheral Opioid Receptors Located on the Rat Saphenous Nerve, *Neuropeptides* 5 217–220 (1984).

Smith et al.; Antinociceptive Models Displaying Peripheral Opioid Activity, *Int. J. Tiss. Reac.* VII:1 61–67 (1985).

Tonussi et al.; Rat knee–joint carrageenin incapacitation test: an objective screen for central and peripheral analgesics, *Pain* 48 421–427 (1992).

Valentino et al.; Receptor Binding, Antagonist, and Withdrawal Precipitating Properties of Opiate Antagonists, *Life Sciences* 32: 25 2887–2896 (1983).

Yuan et al.; Clinical Trials and Therapeutics; the safety and efficacy of oral methylnaltrexone in preventing morphine–induced delay in oral–cecal transit time, *Clinical Pharmacology & Therapeutics* 61:4 467–474 (1997).

PDR Supplement A on Trexan A17–A18 (1994).

* cited by examiner

METHODS FOR TREATING OPIATE INTOLERANCE

RELATED APPLICATION INFORMATION

This application claims the benefit of United States Provisional Application No. 60/150,739, filed Aug. 25, 1999, which is incorporated by reference herein in its entirety.

FIELD OF THE INVENTION

The present invention provides compositions and methods for inducing analgesia, in particular, for treating opiate intolerance associated with opiate analgesics.

BACKGROUND OF THE INVENTION

Therapeutic analgesic doses of morphine, as well as other opiate analgesics, provide pain relief that is often accompanied by a number of unpleasant side effects, such as nausea, vomiting, and constipation. Use of higher doses of narcotics in surgery to supplement hypnotic anesthesia, for example morphine, fentanyl, sufentanyl, alfentanyl or remifentanyl, may cause unwanted bradycardia and hypotension that can complicate the surgical procedures or the recovery. In the postoperative setting, emesis is reduced but not completely controlled by ondansetron, granisetron, dolagetron, metaclopramide and other serotonin receptor antagonist based anti-emetics. Emesis can still be a problem when patients are sensitive to opiate side effects and opiates are used as part of the surgical anesthesia, or used postoperatively to control pain. An agent to selectively block opiate intolerance with minimal side effects would improve medical treatment, either used by itself, or in combination with opiates, or in combination with existing anti-emetic drugs in treating opiate intolerance and post surgical emesis.

Studies with quaternized opiate antagonists, such as N-methylnalorphine, indicate that the quaternized opiate antagonists do not penetrate the blood-brain barrier into the brain. The analgesic effects of opiates are mediated by receptors in the central nervous system, while the opiate receptors that mediate many unwanted opiate side effects lie outside the blood brain barrier. Thus, quaternized opiate antagonists can antagonize many unwanted side effects of opiates without reducing analgesia. For example, studies of N-methylnalorphine, which is a mixture of the R and S isomers, have shown that it antagonizes opiate induced constipation, bradycardia, and emesis at doses that do not alter the ability of opiate agonists to reduce pain.

The S and R isomers of N-methylnalorphine, which are alternatively referred to as the axial and equatorial isomers, have been described as opiate antagonists in the literature, but to date the isomers have only been tested separately in in vitro studies or by a test involving direct injection onto brain. The in vitro studies used receptor binding and isolated tissues to define the range and nature of the receptor interactions, characterizing both isomers as opiate antagonists with reduced potency relative to nalorphine. In addition to a predominant opiate antagonist effect, the S isomer was characterized as having very weak agonist properties in guinea pig ileum but not other tissues with mu receptors, such as the vas deferens (Kobylecki et al., (1982) *J. Med. Chem.*, 25, 1280–1286). The authors speculated that the agonist effects were not mediated by mu opiate receptors.

The two isomers of N-methylnalorphine have also been compared by directly injecting them into the brain of mice. Both isomers antagonized morphine analgesia in the range of 0.25 to 0.5 ug per mouse brain (Iorio et. al., (1984) *Eur. J. Med. Chem.*, 19, 11–16). The weak agonist properties of the S isomer were also apparent at very high doses. Both agents were able to antagonize morphine analgesia by injection into brain. The meaning of this study for medical use of these substances is difficult to determine, however, since quaternized agents do not enter the brain, nor do they antagonize morphine analgesia if given by conventional medical routes of administration. Indeed, it would not be desirable to administer these compounds directly to the central nervous system, thereby antagonizing the analgesic effects of opiates.

As far as the present inventors are aware, there have been no published studies that suggest therapeutically significant differences in the pharmacology of the R and S isomers of N-methylnalorphine in intact mammals using medically appropriate routes of administration.

SUMMARY OF THE INVENTION

It has now surprisingly been found that the essentially pure R isomer of N-methylnalorphine provides a superior treatment to antagonize or prevent opiate induced side effects in mammals, and to have a significantly reduced ability to produce side effects such as nausea, vomiting, and ataxia, when compared with the S isomer or a mixture of R and S N-methylnalorphine.

Accordingly, one aspect of the present invention is a method of treating opiate intolerance in a subject in need of such treatment, comprising administering to the subject a treatment effective amount of R N-methylnalorphine or a pharmaceutically acceptable salt thereof. The opiate intolerance may be manifested by nausea, vomiting, constipation, hypotension, bradycardia, and/or pruritus, or other side-effects associates with opiates, as are known in the art. The active compound can be administered by any route but is preferably administered by intravenous, subcutaneous or intramuscular injection. Administration by a patient-controlled injection device is also preferred. More preferably, the opiate analgesic and the active compound are co-administered in a single composition using a patient-controlled injection device. As a further alternate embodiment, the active compound can be administered concurrently with other therapeutic agents, e.g., an anti-emetic compound.

As a further aspect, the present invention provides a method of inducing analgesia in a subject in need of such treatment, comprising administering to the subject an opiate analgesic in an amount effective to induce analgesia in the subject concurrently with R N-methylnalorphine or a pharmaceutically acceptable salt thereof in an amount effective to treat opiate intolerance. Preferably, concurrent administration of the active compound does not substantially reduce opiate analgesia in the subject.

As yet a further aspect, the present invention provides a composition, comprising, in combination in a pharmaceutically acceptable carrier, an opiate analgesic in an amount effective to induce analgesia in a subject and R N-methylnalorphine or a pharmaceutically acceptable salt thereof in an amount effective to treat opiate intolerance. In particular embodiments, the composition comprises other therapeutic compound(s), e.g., an anti-emetic compound.

These and other aspects of the present invention are provided in more detail in the description of the invention below.

DETAILED DESCRIPTION OF PREFERRED EMBODIMENTS

Figure 1:
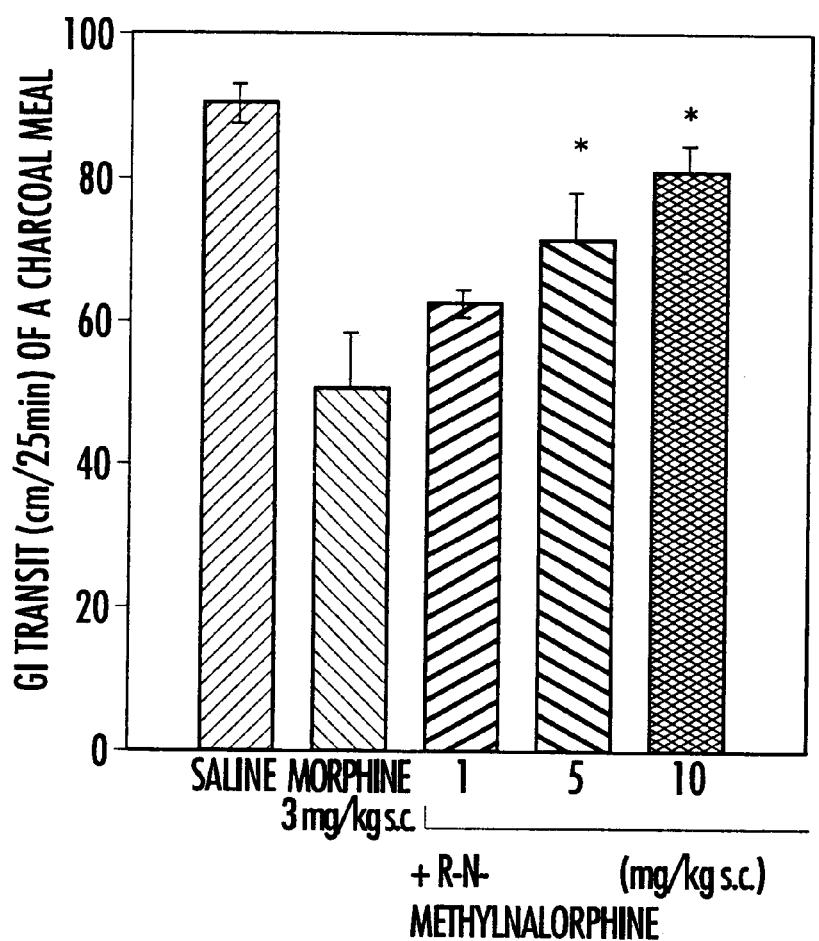
FIG. 1 is a graphical representation of the dose-dependent increase in gastrointestinal transit by R N-methylnalorphine in mice treated with morphine following a charcoal meal. Animals were give R N-methylnalorphine, then morphine 15 minutes later, followed by charcoal suspended in MC. Transit was measured 25 minutes after charcoal. * p<0.05 compared to morphine-treatment.

This present invention is based, in part, on the unexpected finding that the R isomer of N-methylnalorphine is the primary active agent contributing to the medically useful pharmacology of N-methylnalorphine for antagonizing the unwanted side effects of opiate analgesics. The R isomer provides a superior treatment, as compared with the S isomer or a mixture of the two isomers, for opiate intolerant mammals who experience the unwanted opiate side effects including nausea, vomiting, hypotension, bradycardia, constipation during the time they are treated with opiate analgesics. Furthermore, the R isomer provides a treatment to antagonize these opiate-induced side effects, preferably without reducing opiate analgesia or producing other symptoms, over a wide range of doses.

It is understood by those skilled in the art that methylation of nalorphine is known to form two N stereoisomers, the R isomer or equatorial N-methylnalorphine of Formula (I) and the S isomer or axial N-methylnalorphine of Formula (II).

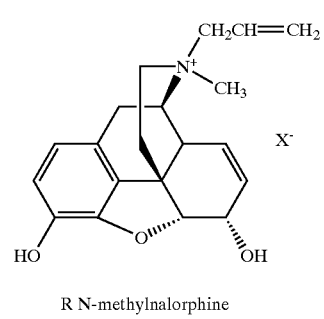

R N-methylnalorphine

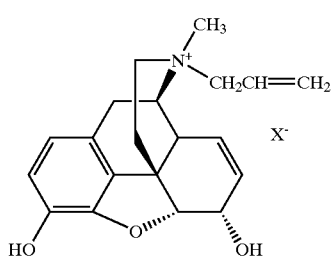

S N-methylnalorphine

The active compound employed herein is R N-methylnalorphine, also called [(5.alpha. ,6.alpha., 17R)-7,8,didehydro-4,5-epoxy-3,6-dihydroxy-17-methyl-17-(2-propenyl)morphinanium], or a pharmaceutically acceptable salt thereof. Such compounds have the structure shown in Formula (I) where the N-allyl group is in the equatorial position, such that the configuration of the chiral N atom is R; X is the anion of an acid, preferably a chloride, bromide, iodide or methanesulfonic anion, and salts and solvates thereof.

Previous in vitro studies have reported that the S isomer is a predominant contributor to the opiate antagonist properties of N-methylnalorphine. Unexpectedly, the present investigations have found that the S isomer does not exhibit useful anti-emetic activity. In fact, emesis, and not protection from emesis, was observed in animals treated with the S isomer. The S isomer of N-methylnalorphine also caused other side effects, such as ataxia and related signs of neurotoxicity. Thus, R N-methylnalorphine may provide a superior treatment for opiate intolerant mammals that experience nausea, vomiting, hypotension, bradycardia, constipation and other side-effects associated with opiate intolerance as are known in the art during the time that opiate analgesics are administered as compared with the S isomer alone or a mixture of the two isomers.

The compound of Formula (I) and salts and solvates thereof may be prepared in any manner known in the art. For example, synthesis of the compound of Formula (I) by the selective quaternization of nalorphine or morphine (the compounds of Formulas (Ill) and (IV), respectively) have been described by K. Koczka and G. Bernath, (1967) Acta Chim. Acad. Sci. Hung. 51, 393–402.

The compound of Formula (I), salts and solvates thereof, may be prepared from nalorphine by a process which comprises:

reacting a compound of Formula (III),

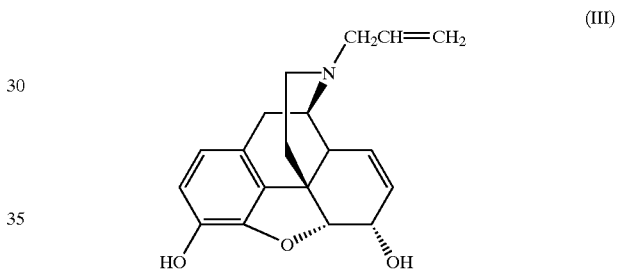

with a methylating agent such as a methyl halide (e.g., methyl iodide, methyl bromide, methyl chloride), a methyl sulfonate (e.g., methyl methanesulfonate, methyl ethanesulfonate, methyl benzenesulfonate, methyl p-toluenesulfate), or a methyl sulfate (e.g., dimethylsufate).

Suitably, the reaction is carried out in a polar solvent such as an alcohol (e.g., methanol, ethanol, 2-propanol) at a non-extreme temperature, such as 0° C. to 100° C., and preferably at 20° C. to 80° C.

The compound of Formula (I), i.e. the R isomer of N-methylnalorphine, may be obtained essentially free of the S-isomer compound by chromatographic separation of the mixture of isomers by preparative high performance liquid chromatography (HPLC) or by fractional recrystallization.

Preparative HPLC may be performed on a preparative YMC Basic Column by elution with deionized water and collection of fractions that contain ultra violet absorbing material. The fractions that contain >99% of the R isomer may be combined, evaporated in vacuo, and converted to the chloride by ion exchange chromatography.

Alternatively, the R isomer may be obtained essentially free of the S isomer of N-methylnalorphine by several recrystallizations of the mixture of isomers from 90% aqueous methanol. The compound of Formula (I) wherein X is the anion of hydrochloric acid, a chloride, may then be formed by ion exchange chromatography.

The compound of Formula (I) may be obtained as the chloride salt by ion exchange chromatography of the bromide or iodide salt by absorption of a hot aqueous solution of the compound of Formula (I) on a hot column of ion exchange resin. The column may be eluted with hot water and the eluate evaporated in vacuo and lyophilized.

As a further illustrative preparative method, the compound of Formula (I) and salts and solvates thereof may be prepared from morphine by a process which comprises: reacting a compound of Formula (IV):

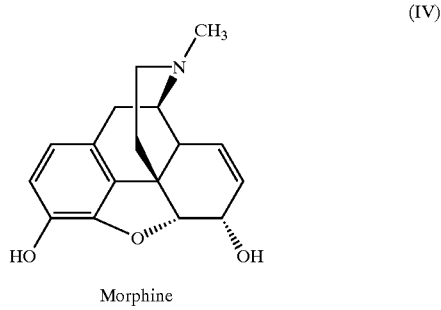

Morphine with an allylating reagent such as an allyl halide (e.g., allyl iodide, allyl bromide, allyl chloride), an allyl sulfonate (e.g., allyl methanesulfonate, allyl ethanesulfonate, allyl benzenesulfonate, allyl p-toluenesulfonate), or an allyl sulfate (e.g., diallylsulfate).

Suitably the reaction is carried out in a polar solvent such as an alcohol (e.g., methanol, ethanol, 2-propanol), or a dipolar aprotic solvent (e.g., N,N-dimethylformamide, dimethylsulfoxide), at a non extreme temperature such as 0° C. to 100° C. and preferably at 20° C. to 80° C.

The R isomer of N-methylnalorphine, i.e., the compound of Formula (I), may be obtained essentially free of the S isomer as described above.

The compound of Formula (I) may be present as a salt, preferably a pharmaceutically acceptable salt. As used herein, the compound of Formula (I) is also preferably present in the salt in a quaternary form. Suitable salts include the anion of acids, preferably, the anion of pharmaceutically acceptable acids. Thus, preferred salts include those formed from the anion of hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic and isethionic acids. An exemplary method of forming the salts of the compound of Formula (I) can be by reacting the compound of Formula (I) in the form of any salt with the anion of the acid in an ion exchange column activated with the anion of the acid.

The compound of Formula (I) can be administered to a subject to treat opiate intolerance (as this term is understood by those skilled in the art) and the unwanted side effects of opiate analgesics (e.g., nausea, vomiting, constipation, hypotension, bradycardia, pruritus, and other side-effects associated with opiate administration as are known by those in the art). In general, it is believed that opiate intolerance results from interaction of the opiate with receptors (e.g., mu receptors) outside of the central nervous system. The terms "treat" or "treating" opiate intolerance as used herein, refer to at least a partial reduction (e.g., diminishment, decrease, mitigation, amelioration) of the negative side-effects associated with the administration of opiate analgesics (as described above) by the administration of the compound of Formula (I). It will be appreciated by those of skill in the art that administration of the compound of Formula (I) may not completely eliminate opiate intolerance or the negative side-effects associated with opiate analgesics. Preferably, administration of the compound of Formula I is carried out so that the benefit outweighs any disadvantages thereof.

Accordingly, a further aspect of the present invention is a method of treating opiate intolerance in a subject comprising administering a treatment effective amount of an active compound containing R N-methylnalorphine or a pharmaceutically acceptable salt thereof. The present invention further provides a method of inducing analgesia in a subject in need thereof by administering an opiate analgesic in an amount effective to induce analgesia in the subject concurrently with an active compound containing R N-methylnalorphine or a pharmaceutically acceptable salt thereof in an amount effective to treat opiate intolerance. Preferably, the concurrent administration of the active compound does not substantially reduce the opiate analgesia (e.g., the dosage sufficient to achieve analgesia is increased by less than 50%, 40%, 30%, 20%, 10%, 5% or less). Alternatively stated, the benefits of the co-administration of the active compound (e.g., in diminishing the negative side-effects of opiate administration) outweigh the detriments (i.e., decrease in opiate analgesia or negative side-effects induced by the active compounds).

The active compound preferably consists essentially of a substantially pure form of the R isomer of N-methylnalorphine, e.g., it is free or essentially free of the S isomer (e.g., is at least about 95%, more preferably at least about 96%, still more preferably at least about 97%, yet more preferably at least about 98%, or still more preferably at least about 99% R isomer).

It is generally accepted in the art that opiate analgesia is the result of opiate binding to receptors (e.g., mu receptors) in the central nervous system, thereby reducing pain in a subject. Accordingly, "opiates" as used herein refers to any compound that binds to opiate receptors (preferably, mu receptors) in the central nervous system of a subject and reduces or diminishes the sensation of pain (e.g., diminishes pain by 25%, 50%, 75%, 85%, 90%, 95%, or even more). Opiates are known in the art and include, but are not limited to, morphine, oxymorphone, codiene, oxycodone, levorphanol, meperidine, propoxyphene, fentanyl, sufentanyl, alfentanil and remifentanil, other structurally-related opiate agonist compounds, and derivatives and pharmaceutically acceptable salts thereof.

The present invention can be carried out for medical or veterinary treatment. Suitable subjects include any animal that is an appropriate subject for opiate administration, as are known by those skilled in the art, i.e., for which opiates provide medically useful analgesia. For example, it is known that opiates are not appropriate for use with feline and equine subjects, which become hyper-excitable and display other behavioral disturbances in response to opiates. Such animals are preferably mammals and include, but are not limited to, primates (e.g., humans, simians, apes), ferrets, canines, ovines, bovines, caprines, porcines, rodents and lagomorphs. More preferably, the animal is a human or a canine subject, most preferably a human subject. Exemplary subjects are those being administered opiate analgesics to control pain associated with cancer, injury, burns, kidney stones, or surgery.

The terms "administration" and "administering" as used herein include both short-term and long-term administration of the formulations described herein. Short-term, or acute, administration can be carried out to respond to relatively short or temporary episodes of pain and/or of opiate intolerance. Alternately stated, acute administration may be carried out for a period lasting for several hours or several days (e.g., two, three or four days). Conversely, long-term or chronic administration of the inventive formulations can be carried out to treat ongoing or relatively long periods of pain and/or opiate intolerance, e.g., as part of an ongoing regime or course of treatment. Alternatively stated, chronic administration may be carried out for a period of many days to a week to many weeks, months, or even years. In preferred embodiments, the inventive formulations are chronically administered.

In preferred embodiments, the opiate analgesic and the active compound containing the R N-methylnalorphine are administered concurrently. By "concurrently", it is meant that the opiate analgesic and the inventive formulations are administered during the same course of treatment, but not necessarily simultaneously. In particular embodiments, the opiate analgesic and the active compound of the present invention are administered essentially at the same time, i.e., within an hour or even minutes of each other. In more preferred embodiments, the opiate analgesic and the formulation are pre-mixed, e.g., as a liquid, and are co-administered to the subject.

Accordingly, the present invention also provides a composition including, in combination, an opiate analgesic and an active compound containing the R isomer of N-methylnalorphine, or a pharmaceutically acceptable salt thereof, in a pharmaceutically acceptable carrier. The active compound is preferably a substantially pure preparation of the compound of Formula (I), i.e., is free or essentially free of the S isomer. The opiate analgesic is preferably present in an amount effective to induce analgesia in the subject, and the active compound is preferably present in an amount effective to treat opiate intolerance. In other preferred embodiments, the opiate analgesic and the formulation containing the active compound are premixed at a predetermined ratio and provided in a single liquid or solid formulation.

In alternate preferred embodiments, the patient self-administers the formulation containing the R N-methylnalorphine, e.g., with a patient-controlled pump or injection device, to control the deleterious side-effects of opiate treatment. Preferably, patient controlled administration of the inventive formulations are in conjunction with patient-controlled administration of an opiate analgesic, e.g., the opiate analgesic and the formulation disclosed herein can be provided in a predetermined ratio in a single solution.

Patient controlled drug delivery devices are known in the art and include, but are not limited to, those described in U.S. Pat. Nos. 5,810,779, 5,795,327, 5,338,157, 5,321,392, 5,085,643, 5,069,668, 5,000,739, 4,828,551, and 5,627,839, which are incorporated herein by reference in their entirety.

Those skilled in the art will appreciate that the inventive formulations can also be administered in conjunction with other therapeutic or pharmaceutical agents. For example, it will often be desirable to administer a subject with both the inventive formulations to control or decrease opiate intolerance and an anti-emetic to control emesis from other sources (i.e., not opiate induced). To illustrate, in a post-operative or cancer treatment setting, an anti-emetic compound(s) may be administered to control emesis that is not associated with opiate administration. Exemplary anti-emetics include the 5HT serotonin receptor antagonists including, but not limited to, ondansetron, dolagetron, dolesetron, metaclopramide and granisetron. The anti-emetic compound(s) and the active compound of the invention may be included together in the same composition.

While it is possible for the compound of Formula (I) and pharmaceutically acceptable salts thereof to be administered as the raw chemical, it is preferable to present them as a pharmaceutical formulation. Formulations of the present invention comprise a compound of Formula (I), as defined above, or a pharmaceutically acceptable salt thereof, together with one or more pharmaceutically acceptable carriers therefor. The carriers are pharmaceutically acceptable in the sense of being compatible with the other ingredients of the formulation and not deleterious to the recipient thereof. The inventive formulations optionally include other therapeutic ingredients, e.g., an opiate analgesic and/or an anti-emetic compound.

Formulations include those suitable for oral, parenteral (including subcutaneous, intradermal, intramuscular and intravenous), rectal and topical (including dermal, buccal, and sublingual) administration although the most suitable route may depend upon, for example, the condition and disorder of the recipient. The formulations may conveniently be presented in unit dosage form and may be prepared by any of the methods well known in the art of pharmacy.

All methods optionally include the step of bringing into association a compound of Formula (I) or a pharmaceutically acceptable salt thereof (active ingredient) with the carrier which constitutes one or more accessory ingredients. In general, the formulations are prepared by uniformly and intimately bringing into association the active ingredients with liquid carriers or finely divided solid carriers or both and then, if necessary shaping the product into the desired formulation. Lipid emulsions may be used in the case of rectal or suppository administration.

Formulations of the present invention suitable for oral administration may be presented as discrete units such as capsules, cachets or tablets, each containing a predetermined amount of the active ingredient; as a powder or granules; as a solution or a suspension in an aqueous medium; or a non aqueous medium or as an oil in water or water in oil liquid emulsion. The active ingredient may also be presented as a paste.

A tablet may be made by compression or molding, optionally with one or more accessory ingredients. Compressed tablets may be prepared by compressing in a suitable machine the active ingredient in a free flowing form, such as a powder or granules, optionally mixed with a binder, lubricant, inert diluent, lubricating agent, surface active or dispersing agent. Molded tablets may be made by molding in a suitable machine a mixture of the powdered compound moistened with an inert liquid diluent. The tablets may optionally be coated, or scored and may be formulated so as to provide slow or controlled release of the active ingredient therein.

Formulations for parenteral administration include aqueous and non-aqueous sterile injection solutions which may contain anti-oxidants, buffers, bacterioistats and solutes which render the formulations isotonic with the blood of the intended recipient, and aqueous and non aqueous sterile suspensions which may include suspending agents and thickening agents. The formulations may be presented in unit-dose or multi-dose containers. For example sealed ampoules and vials, and may be stored in a freeze dried (lyophilized) condition requiring only the addition of the sterile liquid carrier, for example water for injection, immediately prior to use. Extemporaneous injection solutions and suspensions may be prepared for sterile powders, granules and tablets of the kind previously described. The drug substance may also be formulated for injection through a patient controlled injection device in combination with opiate drugs.

Formulations for rectal administration may be presented as suppository with the usual carriers such as cocoa butter or polyethylene glycol.

Formulations for topical administration in the mouth, for example, buccal or sublingual administration, include lozenges comprising the active ingredient in a flavored basis such as sucrose and acacia or tragacanth and pastilles comprising the active ingredient on a basis such as gelatin and glycerin or sucrose and acacia. Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents, or those suitable for parenteral administration in patient controlled injection devices may include stabilizers.

Tablets or other forms of presentation in discrete units may conveniently contain an amount of compound of the Formula (I) which is effective for each of the above mentioned indications at the specified dosage, or as a multiple of the same. For instance, most uses may involve units containing 1 mg to 400 mg, usually between 5 and 100 mgs.

The compound of Formula (I) is preferably used as a treatment or preventative for unwanted side effects caused by opiate analgesic compounds that may be given by all acceptable routes of administration. The dose employed will depend on a number of factors, including the age and sex of the patient, the route and amount of opiate medication administered, and the side effect being treated and its severity. Also the route of administration is likely to vary depending on the medical condition of the patient and its severity.

The compound of Formula (I) may be administered to the patient either enterally or parenterally, depending on the method of opiate treatment and the condition being treated. The preferred method of administration in acute critical care situations is by intramuscular or subcutaneous injections, or by intravenous infusions where the drug is given before or during treatment with opiates to control pain or induce anesthesia. The compound of Formula (I) may be used to treat opiate induced acute nausea, vomiting, bradycaria, and hypotension by parenteral routes. Oral and suppository treatment may be used as a premedication and preventative for surgical applications of opiates, and more likely, for the chronic use of opiate drugs in the treatment of chronic pain, such as in cancer patients.

For each of the above mentioned indications the compound of Formula (I) may preferably be administered at a range of 0.11 to 20 mg/kg per day. The dose range for adult humans is generally from about 70 to 1400 mg/day and preferably 140 to 700 mg/day, although more severe symptoms may require higher doses. It may also be advantageous to administer an initial dose of 200 to 2000 mg the first day followed by lower doses on the second and subsequent days of chronic treatment.

Formulations of the compound of Formula (I) may optionally contain an opiate analgesic. Doses of opiate analgesics are known in the art (see, e.g., Physicians Desk Reference (53d ed. 1999) (www.pdr.net); Goodman & Gilman's The Pharmacological Basis of Therapeutics ($9^{th}$ ed. 1996), McGraw-Hill, N.Y.). Those skilled in the art will appreciate that the dose of the opiate analgesic to be administered will vary with the mode of administration, age and condition of the subject, gender, body weight, etc. Typical doses of the opiate analgesics to be administered to a human subject (adult; 70 kg body weight) by various routes of administration are provided in Table 1. Those skilled in the art will appreciate that doses can be calculated for subjects of different body weights based on the values in Table 1. Moreover, the doses in Table 1 are for adults, doses for pediatric subjects can be determined by routine methods known to those skilled in the art.

TABLE 1

Preferred Doses of Opiates for
Administration with R N-methylnalorphine to Humans

| DRUG | ROUTE | PREFERRED DOSE (mg/70 kg BW adult, unless noted otherwise) |
|---|---|---|
| Morphine | IV | 2 to 15 |
|  | IM | 5 to 20 |
|  | SC | 5 to 20 |
|  | Oral | 40 to 80 |
| Meperidine | IV | 10 mg/ml infused until desired effect (@ 10 to 25 mg) |
|  | IM | 50 to 100 |
|  | SC | 50 to 100 |
|  | Oral | 75 to 200 |
| Fentanyl | IV | 0.002 to 0.005 mg/kg over 2 min. and infusion to maintain desired effect |
|  | IM | 0.5 to 1 |
| Sufentanyl | IV | adults individualized with infusion of 1 to 2 $\mu$g/kg |
| Alfentanyl | IV | 0.5 to 3 $\mu$g/kg/min infused |
| Remifentanyl | IV | Continuous IV infusion 0.1 to 0.25 mg/kg/min to desired effect |
| Hydromorphone | Im | 1 to 4 |
|  | Sc | 1 to 4 |
|  | Oral | 2 to 8 |
| Oxymorphone | IM | 0.5 to 2 |
|  | SC | 0.5 to 2 |
|  | Oral | 5 to 8 |
| Codeine | IM | 100 to 150 |
|  | Oral | 100 to 360/day |
| Oxycodone | Oral | 5–10 |
| Hydrocordone | Oral | 5 to 10 |
| Levorphanol | IM | 1 to 3 |
|  | SC | 1 to 3 |

Likewise, the inventive formulations may additionally contain an anti-emetic compound. Doses of anti-emetic compounds are known in the art (see, e.g., Physicians Desk Reference (53d ed. 1999) (www.pdr.net); Goodman & Gilman's The Pharmacological Basis of Therapeutics ($9^{th}$ ed. 1996), McGraw-Hill, N.Y.). Doses of anti-emetic compounds to administer according to the present invention can be determined by those skilled in the art by routine methods. Typical dosages of various 5-HT serotonin receptor inhibitors for combatting emesis for humans by intravenous or oral administration are provided in Table 2. Those skilled of the art will appreciate that doses can be calculated for subjects of different body weights based on the values in Table 2. Moreover, the doses in Table 2 are for adults, doses for pediatric subjects can be determined by routine methods known to those skilled in the art.

TABLE 2

Preferred Doses of 5-HT Inhibitors and other Antiemetics
to Administer with R N-methylnalorphine to Humans

| DRUG | ROUTE | PREFERRED DOSE (mg/70 kg BW adult unless indicated otherwise) |
|---|---|---|
| Ondansetron | IV | 4 mg over 2–5 min and then as needed up to 40 mg |
|  | IM | 30–40 |
| Granisetron | IV | .04–3 |

TABLE 2-continued

Preferred Doses of 5-HT Inhibitors and other Antiemetics
to Administer with R N-methylnalorphine to Humans

| DRUG | ROUTE | PREFERRED DOSE (mg/70 kg BW adult unless indicated otherwise) |
|---|---|---|
| Dolasetron | IV | 12–100 |
|  | Oral | 25 to 200 |
| Metoclopramide | Oral | 5–50 |
|  | IV | 5–20 |

The following Examples are provided to illustrate the present invention, and should not be construed as limiting thereof. The abbreviations used in the Examples are defined as follows: the term "g" means gram, the term "kg" means kilogram, the term "mg" means milligram, the term "mL" means milliliter, the term "mmol" means millimole, the term "M" means molar, the term "h" means hour, the term "iv" means intravenous, the term "sc" means subcutaneous, the term "im" means intramuscular, and the term "mp" means melting point.

EXAMPLE 1

Preparation of R N-Methylnalorphine [(5.alpha., 6.alpha.,17R)-7,8-didehydro-4,5-epoxy-3,6-dihydroxy-17-methyl-17-(2-propenyl)morphinanium chloride] from Nalorphine Method A. Nalorphine (3.0 g, 9.6 mmol) and methyl iodide (3.0 g, 22 mmol) in methanol (30 mL) was refluxed for 3 h. The reaction mixture was evaporated to dryness, and the residue was recrystallized from 90% aqueous methanol to give 3.4 g (75% yield) of R N-methylnalorphine, the compound of Formula (I), as the iodide salt as platelet crystals, mp 246° C. (dec.), which was nearly completely homogeneous R isomer of N-methylnalorphine [(5.alpha., 6.alpha., 17R)-7,8-didehydro-4,5-epoxy-3,6-dihydroxy-17-methyl-17-(2-propenyl)morphinanium iodide]. Three recrystallizations from 90% aqueous methanol gave platelets of mp 255–256° C. that did not contain any of the S isomer of N-methylnalorphine of Formula (II). (K. Koczka and G. Bernath, (1967) Acta Chim. Acad. Sci. Hung., 51, 393–402).

Method B. Nalorphine hydrochloride (Sigma) (4.75 g, 13.7 mmol) was dissolved in deionized water (50 mL) and combined with chloroform (75 mL) and concentrated ammonium hydroxide (3 mL) in a separatory funnel. The layers were separated, and the aqueous portion was twice extracted with chloroform (74 mL and 20 mL). The combined extracts were dried (anhydrous sodium sulfate), filtered and the volatiles removed by spin evaporation. The residue was dissolved in methanol (50 mL), methyl iodide (Mallinckrodt) (9.0 g, 63.4 mmol) was added, and the securely stoppered reaction flask was heated on a 60° C. oil bath for 4.5 h. The reaction mixture was cooled to 0° C., and the volatiles were removed by spin evaporation. The resultant residue was triturated with acetone (100 mL) at ambient temperature for 0.5 h. The solids were collected, washed with diethylether (20 mL) and dried in vacuo at 40° C. to give a white solid. The solid was recrystallized from deionized water (68 mL), collected, washed with water (5 mL) and dried in vacuo at ambient temperature to give 4.70 g of crude R N-methylnalorphine as the white iodide salt. The iodide salt was dissolved in hot water and applied on a hot column of ion exchange resin (Dowex 1×8–50 chloride resin) (Aldrich) (22 g) and eluted with hot water (500 mL). The column eluate was reduced in volume to 100 mL by spin evaporation in vacuo and than lyophilized to give 3.73 g (71% yield) of R N-methylnalorphine [(5.alpha.,6.alpha., 17R)-7,8-didehydro-4,5-epoxy-3,6-dihydroxy-17-methyl-17-(2-propenyl)morphinanium chloride] as an off white solid, which was 86% pure R isomer of 98.4% purity by HPLC analysis.

Anal. Calcd. $C_{20}H_{24}NO_3Cl$ 1.25 $H_2O$: C, 62.49; H, 6.95; N, 3.64; Cl, 9.22. Found: C, 62.36; H, 6.93; N, 3.72; Cl, 9.21.

Method C. The compound of Formula (I) of greater than 99% purity was prepared by preparative HPLC chromatography. A preparative YMC Basic Column (1000 mm×50 mm) was equilibrated in deionized water. An aqueous solution of a mixture of R N-methylnalorphine and S N-methylnalorphine was applied to the column and eluted with deionized water at a flow rate of 75 mL per min.

The column effluent was monitored by ultra violet at a wavelength of 280 nm. Several 100 mL fractions were collected and analyzed by HPLC using a Waters Symmetry C8 column; 280 nm detection; 1 mL per min flow rate; mobile phase (98-2: 0.1 N aqueous trifluoroacetic acid-acetonitrile). Typical retention times were: R N-methylnalorphine (10–11 min); S N-methylnalorphine (7–8 min); morphine (2–3 min). The fractions that contained >99% R N-methylnalorphine were combined, and the total volume was reduced to less than 100 mL by spin evaporation at 45° C. The white solid was collected, washed with acetone and dried in vacuo. This bromide or iodide salt was converted to the chloride salt by ion exchange chromatography as described in Method B (above) to give R N-methylnalorphine [(5.alpha.,6.alpha.,17R)-7,8-didehydro-4,5-epoxy-3,6-dihydroxy-17-methyl-17-(2-propenyl)morphinanium chloride] as an off white solid that was >99% pure.

EXAMPLE 2

Preparation of R N-Methylnalorphine [(5.alpha.,.6.alpha.,17R)-7,8-didehydro-4,5-epoxy-3,6-dihydroxy-17-methyl-17-(2-propenyl)morphinanium chloride] from Morphine Allyl bromide (Aldrich) (318 g, 2.63 mol) was added in one portion to a stirred solution of morphine (Penick) (150 g, 0.53 mol) and methyl ethyl ketone (Aldrich) (3 L) at 60° C. The reaction was heated at 70° C. for 3 h and at 65° C. for 16 h and then cooled to 40° C. The product was collected by filtration, washed with acetone (1 L) and dried in vacuo at 40° C. to give 204 g (95% yield) of a mixture of R N-methylnalorphine and S N-methylnalorphine in a ratio of 30:70 (analyzed by HPLC method described in Method C, Example 1). This mixture was dissolved in hot deionized water (3L), and the dark solution was allowed to cool. The solids were collected by filtration, washed with deionized water (150 mL) and acetone (0.5 L). The combined aqueous wash and aqueous filtrates, which contained a mixture of R N-methylnalorphine and S N-methylnalorphine in a ratio of 44:56, were reduced in volume to about 1 L by spin evaporation in vacuo. The resultant mixture was heated to reflux to give a solution. Upon cooling crystallization occurred, and the solids were collected and washed with deionized water (50 mL) and with acetone (100 mL).

The combined aqueous wash and aqueous filtrates, which contained a mixture of R N-methylnalorphine and S N-methylnalorphine in a ratio of 56:44, were reduced in volume to about 500 mL by spin evaporation in vacuo. The mixture was heated to reflux to give a solution. Upon cooling crystallization occurred, and the solids were collected by filtration and washed with deionized water and discarded. The combined aqueous wash and aqueous filtrate contained a mixture of R N-methylnalorphine and S N-methylnalorphine in a ratio of 67:33. This aqueous solution was processed by preparative HPLC chromatography as described in Method C (Example 1) to give R N-methylnalorphine as the bromide salt as an off white solid that was >99% pure. The white bromide was converted to the chloride salt by ion exchange chromatography as described in Method B (Example 1) to give R N-methylnalorphine [(5.alpha.,.6.alpha., 17R)-7,8-didehydro-4,5-epoxy-3,6-dihydroxy-17-methyl-17-(2-propenyl)morphinanium chloride] as an off white solid that was >99% pure.

Anal. Calcd. $C_{20}H_{24}NO_3Cl$ $2.8H_2O$: C,58.26;H, 7.24; N, 3.40; Cl, 8.60. Found: C, 58.29; H, 7.28; N, 3.38; Cl, 8.64.

EXAMPLE 3

Pharmaceutical Compositions

In the following compositions, the active ingredient may be any compound of Formula (I) or a pharmaceutically acceptable salt thereof. The described compositions are not intended to be exhaustive, but are presented to illustrate particular formulations for administering R N-methylnalorphine to a subject.

a. Tablet Composition
Example of a 100 mg Compression Coated Tablet:

| | Ingredients | Amount per Tablet |
|---|---|---|
| Core | Active ingredient | 100 mg |
| | Cornstarch | 25 mg |
| | Magnesium Stearate | 2 mg |
| Coating | Coating Lactose | 320 mg |
| | Cornstarch | 50 mg |
| | Gelatin | 6 mg |
| | Magnesium Stearate | 4 mg |

The active ingredient and starch are granulated with water and dried. Magnesium stearate is added to the dried granules. Lactose and starch are granulated with 10% w/v aqueous solution of gelatin and dried magnesium stearate is added to the dried granules. The granulated core is compressed with the granulated coating in a conventional compression-molding machine.

b. Capsule Composition
Example of a 100 mg Capsule:

| Ingredient | Amount per Capsule |
|---|---|
| Active ingredient | 100 mg |
| Lactose | 100 mg |
| Cornstarch | 100 mg |
| Magnesium stearate | 10 mg |

The active ingredient, lactose, cornstarch, and magnesium stearate are brought into intimate admixture with one another and 310 mg of the resultant mixture is introduced into a size 0 hard gelatin capsule.

c. Injectable Composition

| Ingredient | Amounts |
|---|---|
| Active ingredient | 200 mg |
| Hydrochloric acid solution or sodium hydroxide solution 0.1 M to pH of 4.0 to 7.0 | 0.1 M |
| Sterile water, q.s. to | 10 ml |

The active ingredient is dissolved in most of the water, and the pH is adjusted to between 4.0 to 7.0. The batch is then made up to volume with sterile water and filtered through a sterile micropore filter into a sterile amber glass vial and sealed with sterile closures and overseals.

d. Suppository

| Ingredients | Amount per suppository |
|---|---|
| Active ingredient | 200 mg |
| Suppository base | q.s. to 2 grams |

The active ingredient, in fine powder from, is dispersed into a little of the molten suppository base at 50° C. The dispersion is incorporated into the bulk of the base at the same temperature, allowed to cool at 42 to 45° C., poured into suitable 2 g suppository molds and allowed to set at 15 to 20° C. Suitable suppository bases are Massa Esterinum C (Henkel International, Dusseldorf Germany) and Witten H Suppository Compound.

e. Dispersible Tablet

| Ingredients | Amount per tablet |
|---|---|
| Active ingredient | 100 mg |
| Corn Starch | 40 mg |
| Primojel (Trade Name for sodium starch) | 50 mg |
| Glycollate (125#m powder) Dicalcium phosphate dihydrate | 50 mg |
| Sodium carboxymethyl cellulose | 2 mg |
| Sodium saccharin | 5 g |
| Microcrystalline cellulose | 50 mg |
| Magnesium stearate | 3 mg |

EXAMPLE 4
Treatment of Emesis in Mammals Caused by Opiate Intolerance without Reducing Analgesia a. Effects on Emesis in Mammals Opiate induced emesis is one of the significant unwanted effects of the acute clinical use of opiates, and a primary indicator of opiate intolerance. The efficacy of the compound of Formula (I), the R isomer of N-methylnalorphine, versus the mixture of R and S isomers of N-methylnalorphine, is demonstrated by tests of the ability of the compound of Formula (I) to prevent opiate induced vomiting in dogs.

In this test, dogs were fed a can of Alpo® dog food and treated 30 minutes later with a clinically analgesic dose of morphine (0.7 mg/kg intramuscularly) used in veterinary practice to control pain. Various doses of different antagonists were given to dogs by the intravenous route 5 minutes prior to an intramuscular injection of morphine and the number of dogs that were emetic was recorded. Table 3 shows that the compound of Formula (I) was the most potent compound of the antagonists tested in preventing morphine-induced emesis with an intravenous $ED_{84}$ of 0.11 mg/kg. The S isomer of N-methylnalorphine was not active in dogs below a dose of 0.5 mg/kg administered intravenously. The S isomer produced emesis in 1 out of 8 animals by itself as its first pharmacological action. The occurrence of emesis at doses that do not control emesis was surprising because the literature indicates that the S isomer of N-methylnalorphine has predominant antagonist activity in vitro with much weaker (10 fold) agonist potency (Kobylecki et al., (1982) *J. Med. Chem.* 25, 1280–1286).

TABLE 3

| Compound | Anti-emetic $ED_{84}$ value[a] |
|---|---|
| R N-methylnalorphine | 0.11 mg/kg i.v. |
| S N-methylnalorphine | Emesis in 12.5% of animals at 0.5 mg/kg i.v. Does not block morphine at 0.5 mg/kg i.v. |
| R and S N-methylnalorphine | 0.26 mg/kg i.v. |
| N-methylnaltrexone | 0.25 mg/kg i.v. |
| N-methylnaloxone | 0.18 mg/k i.v. |

[a]$ED_{84}$ is the estimated dose that protects 84% of treated dogs from morphine-induced emesis.

b. Effects on Opiate-Induced Analgesia

The clinical use of an opiate antagonist to treat opiate intolerance would depend on the ability of the medication to control signs of opiate intolerance but not prevent adequate pain control. The efficacy of the R isomer of N-methylnalorphine as compared with the mixture of the R and S isomers of N-methylnalorphine, as well as a number of other quaternized opiate antagonist compounds, was demonstrated by comparing the $ED_{84}$ of each compound to protect dogs from the emetic effects of morphine to the minimal effective dose of the compound that antagonizes the analgesic effects of morphine in the tail flick test in rats. The antagonism of the analgesic effects of morphine are an undesirable side effect because the clinical use of these compounds is to control opiate intolerance without effecting analgesia.

The tail flick test in rats is conducted by focusing a heat lamp beam on the rat's tail and recording the time taken for the rat to flick its tail out of the focused light beam. An opiate agonist, such as morphine, causes the rat to leave its tail in the beam longer than untreated animals and reflects the analgesic effects of the opiate. Opiate antagonists, such as nalorphine, prevent the analgesic effects of morphine. Table 4 shows that very high doses of the compound of Formula (I) by the intravenous route were required to reduce morphine analgesia relative to the doses that controlled emesis shown in Table 3. This indicates that the compound of Formula (I) will be the least toxic of the compounds tested for clinical use to control opiate intolerance.

TABLE 4

| Compound | Minimum Effective Dose to Antagonize Morphine Analgesia[a] |
|---|---|
| R N-methylnalorphine | 30.0 mg/kg i.v. |
| S N-methylnalorphine | Not tested above doses causing emesis[b] |
| R and S N-methylnalorphine | 30 mg/kg i.v. |
| N-methylnaltrexone | 15 mg/kg i.v. |
| N-methylnaloxone | 2.5 mg/kg i.v. |

[a]The minimal effective dose was the lowest dose significantly antagonizing the analgesic effects of morphine in the tail flick test.
[b]The S N-methylnalorphine was not tested for antagonism of analgesia because it was not anti-emetic at the doses tested, and dogs demonstrated emesis at doses greater than 0.5 mg/kg.

EXAMPLE 5

Reduced Side Effects of the R Isomer of N-Methylnalorphine over an Extended Dose Range Treatment of opiate intolerance in patient controlled analgesic and outpatient settings strives to maintain the pain control of the opiate and eliminate any other unwanted effects of both the drug used for treatment for opiate intolerance, as well as the nausea, cardiovascular and other opiate-induced side effects. The occurrence of any of these symptoms may prolong the stay in the clinic detracting from the advantages of outpatient treatment.

This Example shows that quaternized opiate antagonists, by themselves, cause ataxic gait (Table 5). Only the opiate antagonist was given to study the acute side effect liability. Relative to the other compounds tested, higher doses of R N-methylnalorphine were required to produce ataxia as compared with the other compounds, with the exception of R and S N-methylnalorphine. Animals showing ataxic gait walked unsteadily with a widespread placement of the feet in a staggering manner.

TABLE 5

| Compound | Minimum Dose to Produce Ataxic Gait In Rat |
|---|---|
| R N-methylnalorphine | 30 mg/kg i.v. |
| S N-methylnalorphine | 15 mg/kg i.v. |
| R and S N-methylnalorphine | 30 mg/kg i.v. |
| N-methylnaltrexone | 15 mg/kg i.v. |
| N-methylnaloxone | 15 mg/kg i.v. |

While all of the antagonists tested in Table 5, including R N-methylnalorphine, produced ataxia after bolus intravenous injection, the greatest therapeutic ratio was obtained for R N-methylnalorphine. The calculation of the therapeutic ratio, a measure of relative safety, was carried out based on the separation of the intravenous doses that protected 84% of emetic mammals, such as dogs from morphine induced vomiting (see Table 3) versus the doses that caused ataxia (see Table 5). The values are shown in Table 6. All of the other compounds had much lower therapeutic ratios in this assay system than did R N-methylnalorphine, indicating that more side effects could be expected accompanying their use during treatment.

TABLE 6

| Compound | Ratio of the Dose Antagonizing Morphine Analgesia Divided by the Dose Protecting Animals from Morphine Induced Emesis |
|---|---|
| R N-methylnalorphine | 273 |
| S N-methylnalorphine | Emetic |
| R and S N-methylnalorphine | 115 |
| N-methylnaltrexone | 60 |
| N-methylnaloxone | 14 |

EXAMPLE 6

Treatment of Opiate Induced Constipation in Mammals

Morphine produces constipation, especially during chronic use. R N-methylnalorphine can also be used to treat constipation. FIG. 1 shows an example where mice were treated with morphine (3 mg/kg s.c.) and given a charcoal meal by oral gavage. These mice had reduced intestinal transit times of the charcoal gavage after morphine. The reduced rate of GI transit time produced by morphine is thought to be the basis of morphine's constipating effects in mammals, including man. Mice given various doses of R N-methylnalorphine had a reversal of the slowed transit time produced by morphine. These results are indicative that R N-methylnalorphine reverses morphine-induced constipation. Tests of a dose of the S isomer of N-methylnalorphine, were found to have no effect on the increased transit time of the charcoal meal produced by morphine, indicating no effect.

EXAMPLE 7

Treatment of Opiate Induced Bradycardia and Hypotension in Mammals

Figure 2:
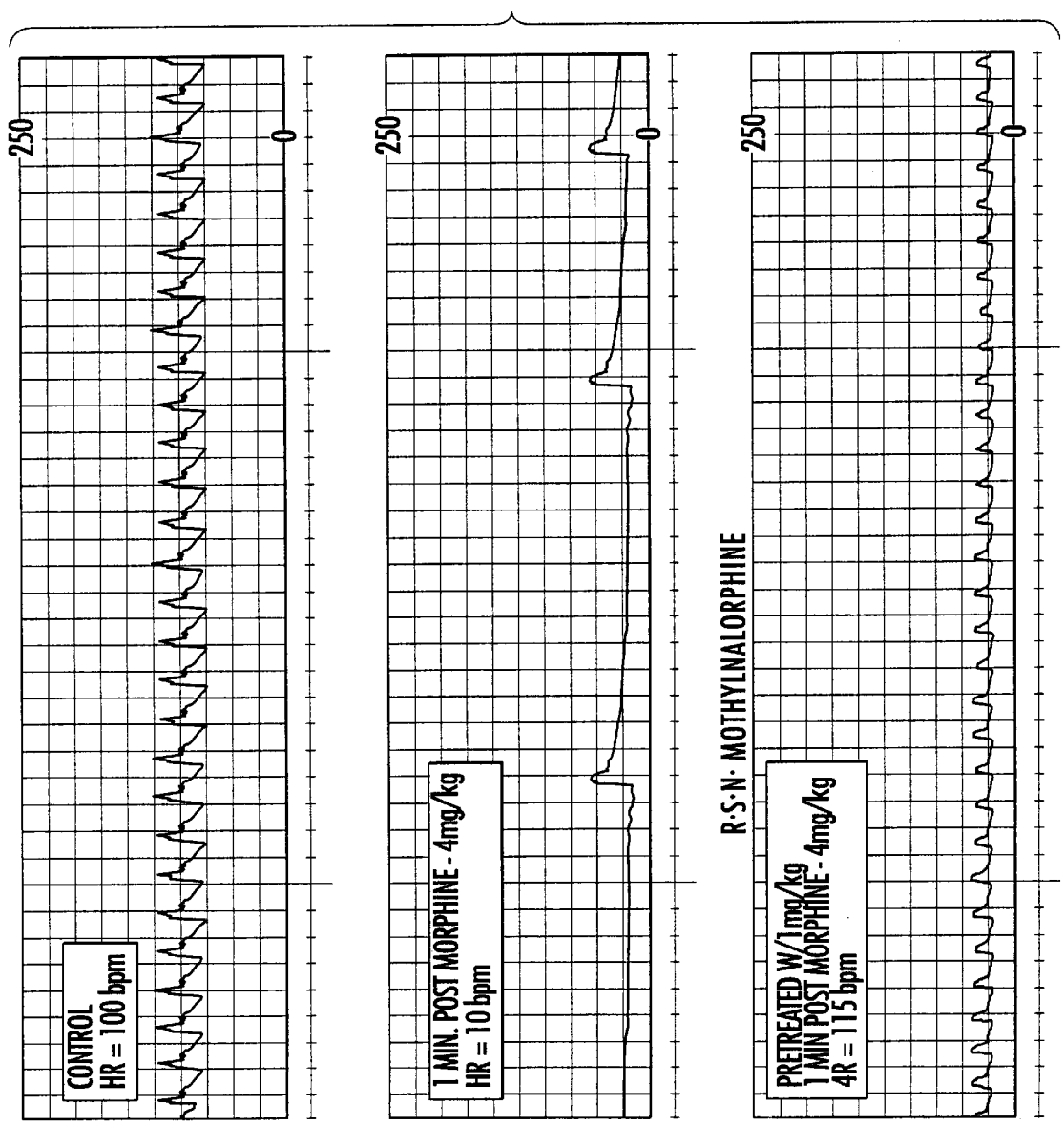
FIG. 2 shows representative electrocardiograms displaying the heart rate of an untreated control dog (top panel), a dog administered with 4 mg/kg morphine i.v. (middle panel), and a dog administered 4 mg/kg morphine i.v. in the presence of 4 mg/kg i.v. of N-methylnalorphine.

Opiates produce unwanted bradycardia and hypotension during surgery when they are given as part of the anesthetic cocktail. The effects of the mixture of R and S isomers of N-methylnalorphine on the bradycardia produced by morphine is shown in FIG. 2. The top panel is the heart-rate of a control, untreated animal, the middle panel is the heart rate 1 min after 4 mg/kg morphine i.v., and the bottom panel is the heart rate of an animal protected by a 4 mg/kg i.v. dose of the mixture of R and S isomers of N-methylnalorphine following injection of the 4 mg/kg i.v. dose of morphine. The mixture of R and S isomers of N-methylnalorphine clearly antagonized the marked bradycardia produced by morphine indicating, by inference, the applicability of R N-methylnalorphine in surgical settings where opiates are used as part of the anesthetic procedure.

The effects of the mixture of R and S isomers of N-methylnalorphine were also tested on blood pressure changes produced by the opiate agonists, morphine and DAGOL (Try.D-Ala,Gly.MePhe.Gly-ol). The mixture of R and S isomers of N-methylnalorphine antagonized the opiate induced hypotension, supporting the use of the pure active R isomer of N-methylnalorphine in anesthetic cocktails to minimize the cardiovascular effects of morphine, fentanyl, sufentanyl, remifentanyl and related opiate anesthetic derivatives during surgery (Clark et al., (1988) *Br. J. Pharmacol.* 95, 275–283).

EXAMPLE 8

Use of N-Methylnalorphine in Combination with Ondansetron and other Antiemetics to Create a Broad Spectrum Antiemetic Formulation for use after Surgery and in Cancer Chemotherapy Ondasetron is used postoperatively to reduce the incidence of emesis during recovery from surgery, and to reduce nausea and vomiting of cancer patients who may be receiving chemotherapy with agents such as cis-platinum. It is not effective in all post surgical or cancer patients. A 0.5 mg/kg i.v. dose of ondansetron that completely protects dogs from cis-platinum-induced emesis failed to protect any dogs from the emetic effects of morphine (0.7mg/kg i.m.), suggesting that the nausea and vomiting produced by morphine treatment of post surgical patients and during cancer chemotherapy would not be prevented by ondansetron alone. In other studies using ferrets, which are also emetic to cis-platinum, a 10 mg/kg i.v. dose of the mixture of R and S isomers of N-methylnalorphine did not block cis-platinum-induced emesis. These findings indicate that the combination of N- methylnalorphine, or just the combination of the R isomer with clinically useful doses of ondansetron, or other anticancer anti-emetic drugs, would provide superior control of emesis compared to either agent alone.

The foregoing is illustrative of the present invention, and is not to be construed as limiting thereof. The invention is defined by the following claims, with equivalents of the claims to be included therein.

I claim:

1. A method of treating opiate-induced emesis in a subject in need of such treatment, comprising administering to the subject a treatment effective amount of a composition comprising R N-methylnalorphine or a pharmaceutically acceptable salt thereof.

2. The method according to claim 1, wherein the opiate-induced emesis comprises a condition selected from the group consisting of nausea, vomiting, and combinations thereof.

3. The method according to claim 1, wherein the subject is one in which opiates provide medically useful analgesia.

4. The method according to claim 1, wherein the subject is selected from the group consisting of human and canine subjects.

5. The method according to claim 1, wherein the subject is a human subject.

6. The method according to claim 1, wherein the R N-methylnalorphine or a pharmaceutically acceptable salt thereof is administered by a route selected from the group consisting of oral, subcutaneous, intradermal, intramuscular, intravenous, rectal, dermal, buccal, and sublingual administration, and combinations thereof.

7. The method according to claim 1, wherein the R N-methylnalorphine or a pharmaceutically acceptable salt thereof is administered by a route selected from the group consisting of intramuscular, subcutaneous, and intravenous administration, and combinations thereof.

8. The method according to claim 1, wherein the R N-methylnalorphine or a pharmaceutically acceptable salt thereof is administered by a patient-controlled injection device.

9. The method according to claim 1, wherein the R N-methylnalorphine or a pharmaceutically acceptable salt thereof is administered in a dose of about 0.11 to about 20 mg/kg/day.

10. The method according to claim 5, wherein the R N-methylnalorphine or a pharmaceutically acceptable salt thereof is administered in a dose of about 70 to about 1400 mg/day.

11. The method according to claim 1, further comprising concurrently administering an anti-emetic compound that does not treat opiate intolerance.

12. The method according to claim 11, wherein the R N-methylnalorphine or a pharmaceutically acceptable salt thereof and the anti-emetic compound are included in the composition.

13. The method according to claim 1, wherein said administering step is a chronically administering step.

* * * * *

UNITED STATES PATENT AND TRADEMARK OFFICE
CERTIFICATE OF CORRECTION

PATENT NO. : 6,455,537 B1
DATED : September 24, 2002
INVENTOR(S) : Cooper

It is certified that error appears in the above-identified patent and that said Letters Patent is hereby corrected as shown below:

<u>Column 10,</u>
Line 38, the last entry in Table 1 should read as follows:

-- Levorphanol     IM    1 to 3
                                SC    1 to 3
                                Oral    2 to 6 --

Signed and Sealed this

Twenty-fifth Day of March, 2003

JAMES E. ROGAN
*Director of the United States Patent and Trademark Office*